United States Patent [19]

Schinabeck et al.

[11] 4,298,753
[45] Nov. 3, 1981

[54] CONTINUOUS PROCESS FOR PREPARING SILANES AND SILOXANES HAVING SiOC GROUPS

[75] Inventors: Anton Schinabeck; Norbert Zeller, both of Burghausen; Tassilo Lindner, Mehring-Öd, all of Fed. Rep. of Germany; Georg Engelsberger, Ach, Austria; Rudolf Riedle, Burghausen, Fed. Rep. of Germany

[73] Assignee: Wacker-Chemie GmbH, Munich, Fed. Rep. of Germany

[21] Appl. No.: 209,447

[22] Filed: Nov. 24, 1980

[30] Foreign Application Priority Data

Jan. 10, 1980 [DE] Fed. Rep. of Germany ....... 3000782

[51] Int. Cl.$^3$ ............................ C07F 7/04; C07F 7/10; C07F 7/18
[52] U.S. Cl. .................................... 556/415; 556/417; 556/440; 556/457; 556/470
[58] Field of Search ............... 556/440, 457, 470, 415, 556/417

[56] References Cited

U.S. PATENT DOCUMENTS 3,244,739 4/1966 Emblem et al. ...................... 556/457
3,651,117 3/1972 Bennett ........................... 556/440 X
3,792,071 2/1974 Nitzsche et al. .................. 556/457 X
4,209,454 6/1980 Graf et al. ........................... 556/457
4,226,793 10/1980 Kötzsch et al. ...................... 556/470

Primary Examiner—Paul F. Shaver

[57] ABSTRACT

A continuous process for preparing silanes and siloxanes having SiOC groups which comprises (a) introducing in a liquid phase a chlorosilane and a hydroxyl-containing aliphatic compound in parallel flow into a first stage of a first reactor in an amount such that from 0.5 to 0.9 gram-mole of hydroxyl group is present per gram-atom of Si-bonded chlorine; (b) removing the liquid reaction mixture from the first reactor; (c) introducing the reaction mixture at the head of a column used as the second reactor which is maintained at an elevated temperature; (d) adding a hydroxyl-containing aliphatic compound as a gas at the lower end of the column or at a point between the lower end and the upper end of the lower one-third of the column, in an amount at least sufficient to completely react with the Si-bonded chlorine present in the reaction mixture obtained from the first stage and (e) removing the silane containing SiOC groups or polysiloxane containing SiOC groups from the column at a point below the point of addition of the hydroxyl-containing aliphatic compound.

5 Claims, No Drawings

CONTINUOUS PROCESS FOR PREPARING SILANES AND SILOXANES HAVING SiOC GROUPS

The present invention relates to a process for preparing silane and siloxanes having SiOC groups and more particularly to a continuous process for preparing alkoxysilanes and alkoxypolysiloxanes.

BACKGROUND OF THE INVENTION

A continuous process for preparing alkoxysilanes or alkoxypolysiloxanes by reacting chlorosilanes with hydroxyl-containing aliphatic compounds and optionally water, in a column maintained at an elevated temperature and equipped with a reflux condenser is described in U.S. Pat. No. 3,792,071 to Nitzsche et al. In this process, the chlorosilane is introduced at the head of the column and the alcohol is introduced in the gaseous form from below or at a point in the lowest one-third of the length of the column and when water is employed, it is introduced at any desired point along the length of the column, and the reaction product is removed from the column at its lower end or at a point below the point of addition of the alcohol.

In contrast to the process described above, the process of this invention provides higher space-time yields without increasing the hydrogen chloride content of the product. Also, undesirable side reactions, such as the polymerization of silanes having aliphatic multiple bonds, are to a great extent avoided in the present process.

Therefore, it is an object of this invention to provide a continuous process for preparing alkoxysilanes and alkoxypolysiloxanes. Another object of this invention is to provide a process for preparing alkoxysilanes and alkoxypolysiloxanes in which the polymerization of silanes having aliphatic multiple bonds is to a great extent eliminated. Still another object of this invention is to provide a process for preparing alkoxysilanes and alkoxypolysiloxanes which are substantially free of hydrogen chloride. A further object of this invention is to provide a process for preparing alkoxysilanes and alkoxypolysiloxanes having higher space-time yields without increasing the hydrogen chloride content of the product.

SUMMARY OF THE INVENTION

The foregoing objects and others which will become apparent from the following description are accomplished in accordance with this invention, generally speaking, by providing a process for preparing alkoxysilanes and alkoxypolysiloxanes which comprises reacting a silicon compound containing an Si-bonded chlorine with an aliphatic compound containing a hydroxyl group and, if desired, water, in a column provided with a reflux condenser and maintained at an elevated temperature, wherein (a) the chlorosilane and hydroxyl-containing aliphatic compound, each in liquid form are introduced in parallel flow into a first state of a first reactor in an amount of from 0.5 to 0.9 gram-mole of hydroxyl group per gram-atom of Si-bonded chlorine; (b) removing the liquid reaction mixture from the first reactor and (c) introducing the mixture to a second stage at the head of a column forming a second reactor which is maintained at an elevated temperature; (d) adding a hydroxyl-containing aliphatic compound as a gas at the lower end of the column or at a point between the lower end and the upper end of the bottom one-third of the column in an amount sufficient to at least react completely with the remaining Si-bonded chlorine in the reaction mixture obtained from the first stage and (e) withdrawing the reaction product from the column at the lower end or below the point where the hydroxyl-containing aliphatic compound is introduced. When water is employed in the process of this invention, it may be introduced in the second stage at any point along the length of the column.

DETAILED DESCRIPTION OF THE INVENTION

Any chlorosilane which has been used or could have been used heretofore in the preparation of silanes containing SiOC groups or siloxanes containing SiOC groups from the reaction of a chlorosilane with a hydroxyl-containing aliphatic compound, and optionally with water, may be used in the process of this invention. The chlorosilanes employed in the process of this invention may be represented by the formula $$R_nSiCl_{4-n}$$

where R, which may be the same or different, represents atoms or organic radicals which are inert towards the particular hydroxyl-containing aliphatic compound used under the particular reaction conditions, and n is 0, 1, 2 or 3.

Suitable examples of R are hydrogen and hydrocarbon radicals such as alkyl radicals, e.g., methyl, ethyl propyl butyl, octyl and octadecyl radicals; alkenyl radicals, e.g., vinyl and allyl radicals; aryl radicals, e.g., the phenyl radical; alkaryl radicals, e.g., the tolyl and xylyl radicals and aralkyl radicals, e.g., the benzyl, phenylethyl and phenylpropyl radicals. The hydrocarbon radicals represented by R may be substituted by atoms or groups which are inert under the reaction conditions, such as halogenoalkyl radicals, in which the carbon atoms to which the halogen is bonded are in the alpha-position, or at least in the gamma-position to the Si atom, for example, the gamma-chloropropyl radical; and haloaryl radicals, for example, the chlorophenyl radicals. Further examples of hydrocarbon radicals substituted by inert groups are the beta-cyanoethyl radical and the gamma-acryloxypropyl radical, as well as the gamma-methacryloxypropyl radical. Because of their availability, it is preferred that n be 0 or 1 and R be a methyl radical. Mixtures of different chlorosilanes can be used. This can be of particular advantage if water is also used in the process of this invention.

Preferably, the chlorosilanes are employed in a liquid form, as long as this requires the minimum expenditure, and preferably the silanes are at room temperature until they enter the column. When water is also used in this process, the chlorosilanes may be diluted with an inert solvent having a boiling point which is higher than the temperature at which the column of the second stage is operated, so that the viscosity of the polysiloxanes having SiOC groups thus formed does not interfere with the removal of the produce from the column.

Any hydroxyl-containing aliphatic compound which could have been used heretofore in the preparation of silanes containing SiOC groups or siloxanes containing SiOC groups by reacting a chlorosilane with a hydroxyl-containing aliphatic compound and optionally with water, and whose boiling points are below that of the particular silane or polysiloxane containing SiOC groups which is being prepared, and which boil at the particular pressure in the column, can also be used as the hydroxyl-containing aliphatic compound in the process of this invention. Preferred alkanols and alkanols substituted with an ether oxygen atom, having from 1 to 6 carbon atoms, which may be used in the process of this invention are methanol, ethanol, beta-methoxy-ethanol, n-propanol and n-hexanol.

It is preferred that the hydroxyl-containing aliphatic compound be used in the first stage in an amount of from 0.7 to 0.9 gram-mole of hydroxyl group per gram-atom of Si-bonded chlorine.

The first reactor, for example, can consist of a vessel equipped with a stirrer or a tube reactor, which can be bent into a ring or can be U-shaped and/or coiled. Furthermore, when a tube reactor is used as the first reactor, the hydrogen chloride formed as a result of the reaction of the compounds introduced into the reactor mixes the reactants and circulates the product in the tube reactor. If desired, however, the contents of the first reactor can also be circulated with a circulating pump. Speeds of from 10 cm to 7000 cm or more per minute can be ued. However, since additional circulation is not required, circulating pumps are not generally used.

Hydrogen chloride is removed from the first reactor at a suitable point, or it may be removed from the reaction mixture obtained from the first reactor and before it enters the second reactor at a point on the pipe between the first and second reactors.

The temperature in the first reactor, as well as the temperature at which the liquid reaction mixture is discharged from the first reactor and introduced at the head of the column used as the second reactor, is preferably from 0° to 20° C. The residence time of the reaction mixture in the first reactor is preferably from 5 to 15 minutes.

Any pipe which can be used for fractional distillations, can be used as the column in the second stage of the process of this invention. Generally, the column is packed with known packing materials such as porcelain saddles or other packing materials. Preferably the column is at least 90 cm long, while the upper limit for the length of the column is generally one of economics. The column used in the second stage of the process of this invention can be equipped with a reflux condenser.

The amount of hydroxyl-containing aliphatic compound which can be introduced into the column used as the second reactor can be equal to the amount of hydroxyl-containing aliphatic compound which is consumed in the reaction with the Si-bonded chlorine remaining in the reaction mixture obtained from the first stage. However, if an excess of hydroxyl-containing aliphatic compound is introduced into the column used as the second reactor, it can be distilled at the reflux condenser and/or withdrawn from the reflux condenser, along with undesirable byproducts, if desired.

When water is used in the process of this invention, it is preferably introduced into the column as a gas. The water can be mixed with the hydroxyl-containing aliphatic compound and introduced into the column, or it can be introduced separately into the column. When water is introduced as a separate stream, it can be introduced into the column at any point other than the point at which the other materials are fed into the column.

When the expression "in the form of a gas" or "as a gas" is used herein in relation to the hydroxyl-containing aliphatic compound and/or with water in the second stage of the process of this invention, it is intended to mean that the hydroxyl-containing aliphatic compound, or water, is introduced at the temperature at which it boils at the prevailing pressure in the column, or above this temperature and in a vaporized state.

The temperature in the column used as the second reactor, at a point approximately 10 cm below the point at which the reaction mixture enters the column from the first reactor, is preferably at least half a degree above the boiling point of the particular alcohol used at the prevailing pressure in the column.

The pressures in the first and second reactors are preferably identical. The process of this invention can usually be carried out at ambient pressure, i.e., at 1 bar or approximately 1 bar, because when the process is operated at the pressure of the ambient atmosphere, the necessity of having to use corrosion-resistant pumps, for example, is eliminated. However, the process can also be carried out at higher or lower pressures, depending on the boiling point of the reactants.

EXAMPLE 1

Into one end of a first reactor consisting of a glass tube bent into a ring, having a length of 1,250 mm and an inside diameter of 100 mm, are introduced in parallel flow 310 moles per hour of vinyltrichlorosilane and 810 moles per hour of ethanol. The temperature of the contents in the tube is 15° C. The liquid reaction mixture discharged from the other end of the glass tube bent into a ring, after the hydrogen chloride is allowed to escape shortly after its discharge from the glass tube, at a point on the line leading to the column used as the second reactor, is introduced at the head of this column. This column is 12,000 mm long and has an inside diameter of 200 mm. It is packed with porcelain saddles (12 mm × 12 mm) for a length up to 10,000 mm. At a point about 9,000 mm below the point at which the reaction mixture from the first reactor enters the column, 120 moles of ethanol are introduced per hour into the column in the form of a gas. The temperature of the contents of the column at a point about 1,000 mm below the point at which the reaction mixture from the first reactor enters the column, is 80° C. The product flowing from the lower end of the column passes through a siphon and a product cooler into a receiver. Almost 310 moles per hour of vinyltriethoxysilane is continuously obtained, having 99.7 percent purity as determined by gas chromatography, and a hydrogen chloride content of less than 5 ppm (parts by weight per million parts by weight).

COMPARISON EXAMPLE (A)

The procedure described in Example 1 is repeated except that the vinyltrichlorosilane and ethanol are introduced into the column without prior reaction with one another in a first reactor. A maximum of 150 moles per hour of vinyltriethoxysilane can be obtained before the hydrogen chloride content of the silane increases to more than 5 ppm.

EXAMPLE 2

The procedure described in Example 1 is repeated except that instead of vinyltrichlorosilane and ethanol, 190 moles per hour of gamma-methacryloxypropyltrichlorosilane and 480 moles per hour of methanol are introduced into the first reactor, and 90 moles per hour of methanol is introduced into the column in the form of a gas. The temperature of the contents of the first reactor is 5° C. At a point 1,000 mm below the point where the mixture from the first reactor enters the column, the temperature of the contents of the column is 66° C.

Almost 190 moles of gamma-methacryloxypropyltrimethoxysilane are obtained having a 99.2 percent purity as determined by gas chromatography and a hydrogen chloride content of less than 5 ppm. The process can be carried out continuously for more than two weeks in the absence of a polymerization inhibitor.

COMPARISON EXAMPLE (B)

About 60 moles per hour of gamma-methacryloxypropyltrichlorsilane are introduced into the column at its head as described in Example 1, and 9,000 mm below this point, 180 moles per hour of methanol is introduced into the column in the form of a gas. After only 8 hours the process must be terminated because the column is plugged with polymer.

EXAMPLE 3

The procedure described in Example 1 is repeated except that, (a) 310 moles per hour of methyltrichlorosilane is used; (b) 310 moles per hour of dimethyldichlorosilane is used; and (c) 310 moles per hour of phenyltrichlorosilane are used instead of the vinyl trichlorosilane. When the dimethyldichlorosilane is used, 540 moles per hour of ethanol are introduced into the first reactor instead of the 810 moles per hour of ethanol, and 80 moles per hour of ethanol are introduced into the column in the form of a gas instead of the 120 moles per hour of ethanol. Each hour, almost 310 moles of methyltriethoxysilane, or 310 moles of dimethyldiethoxysilane, or 310 moles of phenyltriethoxysilane are obtained, each having a purity of more than 99 percent and a hydrogen chloride content of less than 5 ppm.

What is claimed is:

1. A continuous process for preparing silanes and polysiloxanes containing SiOC groups which comprises (a) introducing in parallel flow a silicon compound having Si-bonded chlorine and a hydroxyl-containing aliphatic compound in a liquid phase, into a first stage of a first reactor in an amount of from 0.5 to 0.9 gram-mole of hydroxyl group per gram-atom of Si-bonded chlorine; (b) removing the liquid reaction mixture from the first reactor; (c) introducing the reaction mixture into a second stage at the head of a column forming a second reactor which is maintained at an elevated temperature; (d) adding a hydroxyl-containing aliphatic compound as a gas to the column at a point between the lower end and the upper end of the lower one-third of the column in an amount sufficient to at least completely react with the remaining Si-bonded chlorine in the reaction mixture obtained from the first stage and (e) removing the reaction product from the column at a point below the point of addition of the hydroxyl-containing aliphatic compound.

2. The continuous process of claim 1, wherein water is added at any point along the column forming the second reactor.

3. The continuous process of claim 1, wherein the temperature of the first reactor is from 0° to 20° C.

4. The continuous process of claim 1, wherein the residence time in the first reactor is from 5 to 15 minutes.

5. The continuous process of claim 1, wherein the temperature of the column used as the second reactor is at least half a degree above the boiling point of the hydroxyl-containing aliphatic compound at a point about 10 cm below the point of addition of the reaction mixture obtained from the first reactor at the prevailing pressure in the column.

* * * * *